US012397026B2

(12) United States Patent
Moille et al.

(10) Patent No.: US 12,397,026 B2
(45) Date of Patent: Aug. 26, 2025

(54) DIETARY SUPPLEMENT

(71) Applicant: SOCIÉTÉ DES PRODUITS NESTLÉ S.A., Vevey (CH)

(72) Inventors: Sophie Moille, Evian-les-Bains (FR); Irma Silva Zolezzi, Carrouge (CH); Edwin Alberto Habeych Narvaez, Lausanne (CH); Nicola Galaffu, Ornex (FR); Bertrand Bourqui, Murist (CH); Sara Colombo Mottaz, La Conversion (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 18/137,752

(22) Filed: Apr. 21, 2023

(65) Prior Publication Data

US 2023/0381252 A1 Nov. 30, 2023

Related U.S. Application Data

(62) Division of application No. 15/573,601, filed as application No. PCT/EP2016/063170 on Jun. 9, 2016, now Pat. No. 11,660,322.

(30) Foreign Application Priority Data

Jun. 11, 2015 (EP) ........................................ 1517552

(51) Int. Cl.
*A61K 35/747* (2015.01)
*A23L 33/00* (2016.01)
*A23L 33/135* (2016.01)
*A23L 33/16* (2016.01)
*A61K 9/00* (2006.01)
*A61K 9/107* (2006.01)
*A61K 9/14* (2006.01)
*A61K 33/26* (2006.01)
*A61K 33/42* (2006.01)
*A61K 35/741* (2015.01)
*A61P 3/02* (2006.01)
*A61P 3/10* (2006.01)
*A61P 7/06* (2006.01)

(52) U.S. Cl.
CPC .......... *A61K 35/747* (2013.01); *A23L 33/135* (2016.08); *A23L 33/16* (2016.08); *A23L 33/40* (2016.08); *A61K 9/0053* (2013.01); *A61K 9/0095* (2013.01); *A61K 9/107* (2013.01); *A61K 9/14* (2013.01); *A61K 9/145* (2013.01); *A61K 33/26* (2013.01); *A61K 33/42* (2013.01); *A61K 35/741* (2013.01); *A61P 3/02* (2018.01); *A61P 3/10* (2018.01); *A61P 7/06* (2018.01); *A23V 2002/00* (2013.01); *A23V 2400/175* (2023.08); *A23V 2400/531* (2023.08); *A23V 2400/533* (2023.08)

(58) Field of Classification Search
None
See application file for complete search history.

(56) References Cited

U.S. PATENT DOCUMENTS

| | | | | |
|---|---|---|---|---|
| 6,812,022 B1 * | 11/2004 | Aonuma | ................. | C05F 11/08 424/93.46 |
| 9,241,923 B2 | 1/2016 | Kuang et al. | | |
| 9,414,621 B2 * | 8/2016 | Benyacoub | .......... | A61K 35/745 |
| 2007/0116699 A1 | 5/2007 | Holsworth | | |
| 2008/0233239 A1 * | 9/2008 | Avramis | ................. | A23C 9/133 426/616 |

FOREIGN PATENT DOCUMENTS

| | | |
|---|---|---|
| CA | 2347891 | 3/2001 |
| CN | 101601421 | 12/2009 |
| CN | 102014673 | 4/2011 |
| CN | 102144670 | 8/2011 |
| CN | 101869141 | 7/2012 |
| CN | 102940037 | 2/2013 |
| CN | 103988863 | 8/2014 |
| EP | 0974269 | 1/2000 |
| EP | 2258217 | 12/2010 |
| WO | 0115714 | 3/2001 |
| WO | 2008113665 | 9/2008 |
| WO | 2009004076 | 1/2009 |
| WO | 2009127566 | 10/2009 |
| WO | 2011023689 | 3/2011 |
| WO | 2011114916 | 9/2011 |
| WO | 201217893 | 12/2012 |
| WO | 2013055439 | 4/2013 |
| WO | 2013055444 | 4/2013 |
| WO | 2013141139 | 9/2013 |
| WO | 2014148910 | 9/2014 |
| WO | 2015121461 | 8/2015 |

OTHER PUBLICATIONS

Sakaguchi et al. Int J Vitam Nutr Res., 2004, 74 (1), pp. 3-9.*
Juana Fernández-López et al(Chemical and technological properties of bologna-type sausages with added black quinoa wet-milling coproducts as binder replacer, Elsevier Food Chemistry 310 (2020) 125936) (Year: 2019).
Navam Hettiarachchy et al (Gelling of Plant Based Proteins, Product Design and Engineering: Formation of Gels and Pastes, First Edition) (Year: 2013).
Qian Guo et al(Microstructure and rheological properties of psyllium polysaccharide gel, Elsevier Food Hydrocolloids 23 (2009) 1542-1547) (Year: 2008).
Alyssa Rimmer (5 New Ways to Use Quinoa, Simply Quinoa) (Year: 2017).
"Email Correspondence with CGMCC", 2021, 2 Pages.

(Continued)

*Primary Examiner* — Vera Afremova
(74) *Attorney, Agent, or Firm* — K&L Gates LLP

(57) ABSTRACT

An oral composition comprising at least one probiotic bacteria selected from the genera: *Lactobacillus*, *Bifidobacterium*, and *Bacillus*, and ferric pyrophosphate.

12 Claims, No Drawings

(56) References Cited

OTHER PUBLICATIONS

"The Chinese General Microbiological Culture Collection Center", Retrieved from (www.cgmcc.net/english/deposit), Nov. 23, 2021, pp. 1-2.
Barrett et al., "Probiotics for Preventing Gestational Diabetes", Cochrane Database of Systematic Reviews, vol. 2, 2014, pp. 1-26.
Lindsay et al., "Prematurity, Physiolgy", American Journal of Obstetrics & Gynecology, 2014, p. S342.
Lindsay et al., "Impact of Probiotics in Women with Gestational Diabetes Mellitus on Metabolic Health: A Randomized Controlled Trial", American Journal of Obstetrics & Gynecology, 2015, pp. 496.e1-496.e11.
Callaway et al., "Probiotics for the Prevention of Gestational Diabetes Mellitus in Overweight and Obese Women: Findings from the Spring Double-Blind Randomized Controlled Trial", Diabetes Care, vol. 42, 2019, pp. 364-371.
Datasheet for the Decision of Case No. T 1941 /12, Dec. 16, 2014, 22 Pages.
"Masterpiece Organic Agriculture Nutrition Powder", Mintel, Record Id 272224, 2004, 2 Pages.
"Student's T-Test", Wikipedia, 2022, 10 Pages.
"Terms and Conditions of Access and use General", 2017, 5 Pages.
"Declaration of Edwin Habeych", May 10, 2022, 2 Pages.
Martinez et al., "Measuring the Potential Impact of New and Reformulated Bread and Breakfast Cereal Products on Nutrient Intakes", United States Department of Agriculture, 2021, pp. 1-25.
Fu et al., "Research Progress of Iron Supplements for Human Body", HeilongJiang Medicine Journal, vol. 19, Issue No. 3, Dec. 31, 2006, pp. 207-208.
Hao et al., "Interventions for Iron Deficiency Anemia", Chinese Journal of Eugenics and Genetics, vol. 14, Issue No. 10, Dec. 31, 2006, pp. 3-5.
Jiang et al., "Iron", Pictorial Book of Health Food, May 31, 2015, pp. 129-132.
Office Action Received for Application No. CN201680029716.1, mailed on Sep. 27, 2020, 21 Pages(8 Pages of English Translation and 13 Pages of Official Copy).
Enlargement of the Six Product Images of Vanilla Mango Flavoured Formulated Milk for Pregnant Women, Mintel, Record ID: 2577737, 2014, 5 Pages.
Application originally filed on Jun. 9, 2016 for PCT Patent Application No. PCT/EP2016/063170, 45 pages.
Sakaguchi et al., "Iron Absorption and Bioavailability in Rats of Micronized Dispersible Ferric Pyrophosphate", International Journal for Vitamin and Nutrition Research, vol. 74, Issue No. 1, 2004, pp. 3-9.
Rossi et al., "Colloidal Iron(III) Pyrophosphate Particles", Food Chemistry, vol. 151, 2014, pp. 243-247.
Enos et al., "Probiotics and Nutrients for the First 1000 Days of Life in the Developing World", Beneficial Microbes, vol. 4, Issue No. 1, Mar. 2013, p. 3-16.
Hummelen et al., "Effect of Micronutrient and Probiotic Fortified Yogurt on Immune-Function of Anti-Retroviral Therapy Naive HIV Patients", Nutrients, vol. 3, Issue No. 10, 2011, pp. 897-909.
Hemsworth et al., "The Development of Micronutrient Supplemented Probiotic Yogurt for People Living with HIV: Laboratory Testing and Sensory Evaluation", Innovative Food Science and Emerging Technologies, vol. 12, Issue No. 1, 2011, pp. 79-84.
"Product data sheet FD-DVS YF-L812 Yo-Flex®", Chr. Hansen, Aug. 12, 2011, 4 Pages.
Notice of Oppostition for Appl No. 1673314.5-1105 dated Jan. 28, 2021.
Choi et al., "Impact of Iron Encapsulation within the Interior Aqueous Phase of Water-in-Oil-in-Water Emulsions on Lipid Oxidation", Food Chemistry, vol. 116, Issue No. 1, 2009, pp. 271-276.
Gueimonde et al., "Viability and Diversity of Probiotic Lactobacillus and Bifidobacterium Populations Included in Commercial Fermented Milks", Food Research International, vol. 37, Issue No. 9, Dec. 31, 2004, pp. 839-850.
"Full Step Advanced Nutritional Supplement", In nova, Product ID: 1766054, Jun. 2014, 2 Pages.
"Anmum Materna Milk Powder for Pregnant Women", In nova, Product ID: 1499535, Jun. 2014, 2 Pages.
"Celia Mama Nutritional Milk Preparation with Vanilla Flavor", Innova, Product ID: 1960070, Feb. 2015, 2 Pages.
"Friso Mum Gold Nutritional Supplement for Pregnant and Breast Feeding Women", Innova, Product ID: 1119373, Mar. 2012, 2 Pages.
"Frisomum Gold Nutritional Supplement for Pregnant Women and Lactating Moms", Innova, Product ID: 1888965, Dec. 2014, 2 Pages.
"Babecare Milk Powder for Pregnant and Lactating Mothers", Innova, Product ID: 1485661, May 2014, 2 Pages.
Notification Receipt China General Microbiological Culture Collection Centre No. 1.3724, Nov. 5, 2004, 1 Page.
European Office Action for Appl No. 16733415.5 dated Jan. 28, 2021.
Written Opinion of the International Searching Authority received for PCT Patent Application No. PCT/EP2016/063170, mailed on Sep. 19, 2016, 3 Pages.
"Vanilla Mango Flavoured Formulated Milk for Pregnant Women", Mintel, Record ID: 2577737, Jul. 2014, 4 Pages.
"Step O Nutritional Supplement for Pregnant and Lactating Women", Mintel, Record ID: 1795506, May 2012, 4 Pages.
"Nutritional Supplement for Pregnant Women & Breastfeeding Mothers", Mintel, Record ID: 1740436, Mar. 2012, 5 Pages.
Wegmuller et al., "Particle Size Reduction and Encapsulation Affect the Bioavailability of Ferric Pyrophosphate in Rats", The Journal of Nutrition, vol. 134, Issue No. 12, 2004, pp. 3301-3304.
Notice of Opposition for Appl No. 16733314.5 dated Jan. 28, 2021.
Hartman-Craven et al., Relative bioavailability of iron and folic acid from a new powdered supplement compared to a traditioanl tablet in pregnant women, BMC Pregnancy and Childbirth, 2009, 9:33.
Fidler et al., A micronsed, dispersible ferric pyrophosphate with high relative bioavailability in man, British Journal of Nutrition, (2004 ), 91, 107-112.
Product Catalogue—Dr. Paul Lohmann (last visited May 22, 2020).
Mayo Clinic, Gestational Diabetes—Symptoms and Causes (pp. 1-7) (last visited Nov. 11, 2019).

* cited by examiner

DIETARY SUPPLEMENT

CROSS REFERENCE TO RELATED APPLICATIONS

The present application is a divisional of U.S. patent application Ser. No. 15/573,601 filed Nov. 13, 2017, now issued as U.S. Pat. No. 11,660,322 on May 30, 2023, which is a National Stage of International Application No. PCT/EP2016/063170 filed Jun. 9, 2016, which claims priority to European Patent Application No. 15171552.1 filed Jun. 11, 2015, the entire contents of which are being incorporated herein by reference.

FIELD OF THE INVENTION

The present invention relates to the provision of a composition, such as a dietary supplement or dietary food, especially for pregnant and/or lactating females. The composition comprises a pro biotic bacteria and a source of iron, wherein the iron source does not cause significant inhibition or reduction in the viability of the bacteria. The composition may be particularly useful for normalising plasma glucose concentrations, increasing insulin sensitivity and thereby reducing the development of gestational diabetes, whilst maintaining sufficient iron levels. The composition may be used as a pre-pregnancy, pregnancy, and/or lactation supplement.

BACKGROUND

During pregnancy, various metabolic effects such as weight gain and changes in the metabolism of glucose and lipids occur in order to support the growth and development of the fetus. However, in some cases, these metabolic changes may result in a long-term effect on the health of the mother and/or the child, such as disturbances in glucose metabolism. In some pregnant women, these changes may result in an impaired glucose tolerance, giving rise to an increased risk of development of gestational diabetes mellitus, and subsequently Type 2 diabetes mellitus. Further, impaired glucose metabolism in a pregnant woman may be associated with risks to fetal outcomes, such as macrosomia, or impaired glucose tolerance with possible development of diabetes mellitus in the child.

WO2009004076 discloses a composition containing pro biotic bacteria for preventing gestational diabetes, improving insulin sensitivity, and/or preventing metabolic syndrome in the infant. The probiotic bacteria can include a lactic acid bacteria (e.g. *Lactobacillus*) and/or a Bifidobacteria. The compositions may, for example, be in the form of a nutritional supplement, which may also contain micronutrients such as vitamins, minerals and trace elements that may be of particular benefit during pregnancy.

A particularly important trace element is iron. Worldwide, iron deficiency is the one of the most prevalent nutrient deficiencies. In humans, iron is essential for the functioning of a large number of biological processes such as: oxygen binding and transport, binding and transport of oxygen, gene regulation, neurological function, immune function, and regulation of cell growth and differentiation. Iron deficiency may result in anemia, as well as a variety of health problems, such as impairment of thyroid, immune and mental functions, physical performance, cognitive development, increased sensitivity to insulin and fatigue.

Iron deficiency is especially widespread in pregnant and lactating women, and in children. For example, as many as over 50% of pregnant women are considered to be anemic. During pregnancy, the growing fetus and the increasing maternal blood volume, imposes a huge requirement for iron. Iron requirements typically increase by about 50% compared with pre-pregnancy requirements. In pregnant women, iron deficiency has been associated with adverse gestational outcomes such as low birth weight, retarded fetal growth, lowered resistance to infection and poor cognitive development, especially if present during early gestation. Further, anemia in pregnancy, which is commonly caused by iron deficiency, has been associated with increased maternal and perinatal mortality and morbidity. For example, iron supplementation during pregnancy has been associated with a lower risk of preterm delivery. Pregnant and lactating women typically need to ingest additional iron in the form of supplements because their normal diet usually will not provide the required amount.

Fortification of foods with iron is one approach to combatting iron deficiency. However, in particularly vulnerable groups, or in groups which require a higher intake of iron, such as in pregnant or lactating females, iron-fortified foods may not provide sufficient iron in order to meet the daily iron requirements in such groups. In view of this, oral iron supplements in order to correct iron deficiencies are typically preferred.

The dietary reference intake (DRI) for iron typically varies from 8 mg iron/person/day for adult men to 18 mg iron/person/day for menstruating women. The DRI is far greater for pregnant women, i.e. 27 mg iron/person/day. For breast-feeding mothers, the DRI is 9-10 mg iron/person/day.

The upper limit for iron is 45 mg iron/person/day for adults ($\geq$19 years of age), and adolescents (14-18 years) and 40 mg iron/person/day for infants (0-12 months) and children (1-13 years).

Therefore, the inclusion of an iron source in dietary compositions or supplements, particular dietary supplements for females pre-pregnancy, during pregnancy and/or during lactation, is highly desirable. A large variety of iron compounds have been used as iron fortifying agents in food products and in nutritional supplements. Iron sources in the form of ferrous or ferric compounds, such as ferrous sulfate, ferric ammonium citrate, and ferrous bisglycinate, are commonly used in oral iron supplements. Ferrous sulfate is the cheapest and most widely used form Ferrous sulfate is very reactive, and has a very high water solubility and therefore a high bioavailability. Owing to its high bioavailability, ferrous sulfate is often used as the standard reference for the assessment of bioavailability of other iron compounds.

However, we have found that a number of iron compounds, when used to fortify a composition containing a probiotic bacteria, have a deleterious effect on the viability of the pro biotic bacteria. In particular, we have found that when combined with a probiotic, these iron compounds were found to cause a significant reduction in the viability of the bacteria. Thus, an object of the present invention is to provide a pro biotic composition containing an iron-fortifying agent, in which the viability of the probiotic bacteria is not compromised.

SUMMARY OF THE INVENTION

We have surprisingly found that ferric pyrophosphate, when used as an iron-fortifying agent in a composition containing probiotic bacteria, does not cause a reduction in the viability of the bacteria.

Thus, in a first aspect, the present invention provides an oral composition comprising: at least one probiotic bacteria selected from the genera: *Lactobacillus, Bifidobacterium,* and *Bacillus,* and ferric pyrophosphate.

The present invention further provides a composition comprising a pro biotic bacteria selected from the genera: *Lactobacillus, Bifidobacterium* and *Bacillus,* and ferric pyrophosphate for use in the treatment or prevention of gestational diabetes, the treatment or prevention of iron deficiency and/or the treatment or prevention of anemia in a pregnant or lactating woman.

A further aspect of the present invention provides the use of ferric pyrophosphate, as an iron-fortifying agent in an oral probiotic supplement.

A still further aspect of the present invention provides the use of ferric pyrophosphate for preserving the viability of pro biotic bacteria in an oral probiotic composition. Preferably, the ferric pyrophosphate is in finely divided form. For example, the ferric pyrophosphate may comprise microparticles, and/or may be in colloidal form, such as an emulsion or a colloidal suspension of solid particles in a liquid.

DETAILED DESCRIPTION OF THE INVENTION

Unless otherwise indicated, references to % relate to weight %.

Unless otherwise indicated, particle size and particle size distributions may be measured by any method appropriate to the sample's size range. For example, laser diffraction may be used, e.g. using a Mastersizer 3000, Malvern Instruments Ltd, Malvern UK.

As used herein, references to the iron source, particularly ferric pyrophosphate, being microparticulate, or being in microparticulate form, means that it comprises mainly microparticles. Microparticles are particles between 0.1 and 100 µm in size. The microparticulate iron source may optionally contain particles smaller than this, for example in the case of ultrafine powders. By the nature of powder production techniques, most powders contain a range of particles sizes and may comprise particles which are agglomerates of smaller particles. Thus, for example, a microparticulate iron source (especially ferric pyrophosphate) may primarily be comprised of microparticles of the iron source, but may also contain a portion of ultrafine particles. The term micronized refers to a process of forming a material into microparticles, for example milling. The ferric pyrophosphate for use in the compositions of any aspect or embodiment of the present invention may advantageously comprise primarily microparticles (e.g. ferric pyrophosphate powder) or may comprise primarily microparticles and a portion of ultrafine particles, wherein the ultrafine particles form a minor component of the composition. A microparticulate iron source may for example be, a ferric pyrophosphate powder from P. Lohmann with a $D_{97}$ of approximately 7 µm or SunActive ferric pyrophosphate emulsion from Taiyo.

As used herein, the term Dx means that x % of the particles (based on volume) has a diameter of or below a specified D value. Thus, by way of example, a $D_{90}$ of 100 µm means that 90% of the particles, by volume, have a diameter of or below 100 µm, and a $D_{97}$ of 100 µm means that 97% of the particles, by volume, have a diameter of or below 100 µm. The term average particle size refers to a mean average particle size, for example the volume mean diameter D4,3 as determined by laser diffraction.

As used herein, the term "pro biotic" refers to microbial cell preparations or components of microbial cells with a beneficial effect on the health or well-being of the host [Salminen S, et al., "Probiotics: how they should be defined", Trends Food Sci. Technol, (1999), 10, 107-10].

Colloids are microscopic dispersions of one phase (the dispersed phase) in another (the dispersion medium), examples include foams, gels, emulsions, and sols. Ferric pyrophosphate in the composition of the invention may be in the form of a colloidal suspension of solid particles or in the form of an emulsion. As used herein, ferric pyrophosphate in the form of an emulsion can include ferric pyrophosphate which mixed with at least one emulsifier such as soya lecithin and fatty acid esters such as poly glycerol fatty acid esters. Particularly ferric pyrophosphate in the form of an emulsion refers to ferric pyrophosphate which is emulsified with hydrolysed soya lecithin and polyglycerol fatty acid ester. For example, such an emulsion of ferric pyrophosphate may contain microparticulate ferric pyrophosphate as the major ferric pyrophosphate component.

Probiotic Bacteria

The probiotic bacteria, i.e. a bacteria preparation with a beneficial effect on the health or well-being of the host, used in the compositions of the present invention can be selected from those of the genera *Lactobacillus, Bifidobacterium* and *Bacillus* that are known to possess pro biotic activity. The probiotic bacteria may be any of the above genera having established pro biotic characteristics having particular regard to adhesion and competitive exclusion properties.

The genus *Lactobacillus* includes various gram-positive, non-spore-forming bacteria of the family Lactobacilloae. *Lactobacillus* are characterized by their ability to produce lactic acid from the metabolism of glucose and other hexose sugars.

Preferred *Lactobacillus* species which are useful in the compositions of the present invention include those selected from the group consisting of: *L. acidophilus, L. casei, L. paracasei, L. rhamnosus, L. delbrueckii* subsp. *bulgaricus, L. brevis, L. johnsonii, L. plantarum, L. fermentum, L. casei* Shirota, and *L. casei rhamnosus. L. rhamnosus* is an especially preferred species. *L. rhamnosus* species (for example *L. rhamnosus* ATCC 53103 (obtainable inter alia from Valio Oy of Finland under the trade mark LGG) and *L. rhamnosus* CGMCC 1.3724 and particularly *L. rhamnosus* CGMCC 1.3724) are known to be beneficial for preventing gestational diabetes, improving insulin sensitivity and/or preventing metabolic syndrome in the infant. *L. rhamnosus* species are also known to have immunomodulatory effects when administered to pregnant and/or lactating females, for example by significantly reducing the risk of allergic response in the offspring.

Of the *L. rhamnosus* species, the preferred strains include those selected from the group consisting of: *L. rhamnosus* CRL1505, *L. rhamnosus* GG, *L. rhamnosus* CGMCC 1.3724, *L. rhamnosus* ATCC 53103 and *L. rhamnosus* NCC 4007, more preferably *L. rhamnosus* ATCC 53103 and *L. rhamnosus* CGMCC 1.3724 and most preferably *L. rhamnosus* CGMCC 1.3724.

The genus *Bifidobacterium* includes various gram-positive non-motile anaerobic bacteria. They are present in the gastrointestinal tract (primarily the colon) in mammals including humans. Preferred species of *Bifidobacterium* that have a probiotic effect, and which are useful in the compositions of the present invention include those selected from the group consisting of: *B. lactis, B. longum, B. breve,* the strain of *Bifidobacterium breve* M-16V sold by Morinaga, and the strain of *Bifidobacterium breve* R0070 sold by Institut Rosell (Lallemand)], *B. infantis, B. adolescentis, B. animalis, B. bifidum, B. lactis, B. longum* (particularly *B.*

*longum* ATCC BM-99, obtainable from Morinaga Milk Industry Co. Ltd. of Japan under the trade mark B8536).

*B. breve* species are particularly preferred, the strain of *Bifidobacterium breve* M-16V sold by Morinaga, and the strain of *Bifidobacterium breve* R0070, sold by Institut Rosell (Lallemand)].

The genus *Bacillus* encompasses Gram positive spore-forming aerobic or facultative aerobic members. *Bacillus* species having probiotic properties, and which are therefore useful in the compositions of the present invention, include: *B. subtilis, B. coagulans, B. subtilis, B. clausii*, B, *pumilus, B. cereus. B. cereus* is a particularly preferred specifies. Of the *B. cereus* species the preferred strains are *B. cereus* NVH 75/95 and *B. cereus* IP 5832.

Suitable pro biotic lactic acid bacteria include *Lactobacillus rhamnosus* ATCC 53103 obtainable inter alia from Valio Oy of Finland under the trade mark LGG and *Lactobacillus rhamnosus* CGMCC 1.3724. Suitable probiotic Bifidobacteria strains include *Bifidobacterium lactis* CNCM 1-3446 sold inter alia by the Christian Hansen company of Denmark under the trade mark Bb12, *Bifidobacterium longum* ATCC BAA-999 sold by Morinaga Milk Industry Co. Ltd. of Japan under the trade mark B8536, the strain of *Bifidobacterium breve* Bb-03, the strain of *Bifidobacterium breve* M-16V sold by Morinaga, and the strain of *Bifidobacterium breve* R0070 sold by Institut Rosell (Lallemand).

Mixtures of one of more of any of the above described probiotics may be used in the compositions of the present invention. For example, the composition may contain a mixture of genera (particularly a combination of *Lactobacillus* and *Bifidobacterium*, or a combination of *Lactobacillus* and *Bacillus*, preferably a combination of *Lactobacillus* and *Bifidobacterium*). The composition may contain a mixture of species of *Lactobacillus, Bifidobacterium*, and *Bacillus*, and/or may also contain a mixture of strains of one or more of these species.

In particular, in any aspect or embodiment of the present invention, the composition may contain a mixture of probiotic lactic acid bacteria, particularly *Lactobacillus*, and *Bifidobacterium*. Thus, a composition according to any aspect or embodiment of the present invention may include *Lactobacillus rhamnosus* CGMCC 1.3724 and *Bifidobacterium lactis* CNCM 1-3446, for example equal quantities of *Lactobacillus rhamnosus* CGMCC 1.3724 and *Bifidobacterium lactis* CNCM 1-3446.

The probiotic bacteria may be present in the compositions of any aspect or embodiment of the present invention, for example, in an amount: ≥5 million, ≥10 million, ≥15 million, ≥20 million, ≥25 million, ≥30 million, ≥35 million, ≥45 million, ≥50 million, ≥75 million, ≥100 million, ≥250 million, ≥500 million, ≥ 750 million, ≥1 billion or ≥2 billion bacteria per dosage form of the present invention. For example the probiotic may be present in amounts of: 5 million to 2500 million, 10 million to 2500 million, 30 million to 2500 million, 50 million to 2500 million, 50 million to 1000 million, 75 million to 2500 million, 75 million to 1000 million, 100 million to 2500 million, 100 million to 1000 million, 250 million to 2500 million, 250 million to 1000 million, 500 million to 2500 million, 500 million to 1000 million, 750 million to 2500 million or 750 million to 1000 million, 1 billion to 2.5 billion, 1.5 to 2.5 billion bacteria per dosage form.

The compositions of the present invention may be formulated in order to provide a daily dose of the pro biotic bacteria of, for example, from 10e3 to 10e14, 10e4 to 10e12, 10e5 to 10e12, 10e6 to 10e12, 10e7 to 10e11, and particularly 10e7 to 10e10 colony forming units (cfu).

The selected pro biotic bacteria may be cultured according to any suitable method and prepared for addition to the composition by known techniques such as freeze-drying or spray-drying for example. Alternatively, bacterial preparations can be bought from specialist suppliers such as Morinaga, Institut Rosell, Christian Hansen and Valio already prepared in a suitable form for addition to food products such as nutritional and infant formulas. The pro biotic bacteria may be added to the composition in an amollilt between 10e3 and 10e12 cfu/g powder, more preferably between 10e7 and 10e12 cfu/g powder.

Ferric Pyrophosphate

We have found that when formulating a composition containing a probiotic bacteria and an iron fortifying agent, some iron fortifying agents are incompatible with the bacteria, causing a loss in bacteria viability, and in particular their ability to replicate. The incompatibility would seem to be independent of the oxidation state of the iron compound, since both ferrous and ferric forms of iron have been found to reduce bacteria viability. For example, we have found that the known iron fortifying agents, ferrous bisglycinate and ferric ammonium citrate, as well as ferrous sulfate, caused a significant loss of bacteria viability. Such an incompatibility is highly undesirable from the point of view of storage stability of the composition and/or preparation of the composition (i.e. reconstitution of the powder into water or other beverage).

Moreover, when the combination of pro biotic and iron compound are ingested in combination, the incompatibility may result in a further loss of activity of the probiotic bacteria in the gastrointestinal tract, thereby further reducing the potency of the probiotic bacteria.

However, we have surprisingly found that ferric pyrophosphate does not decrease bacterial viability in probiotic bacteria. Surprisingly, we have found that finely divided forms of iron fortifying agents, for example ferrous pyrophosphate, do not decrease bacterial viability. The finely divided forms of ferric pyrophosphate are particularly advantageous for the present compositions they have the additional advantage of having a high bioavailability in addition to their biocompatibility with the pro biotic bacteria. It is surprising that finely divided forms of ferric pyrophosphate, such as those comprising microparticles, do not decrease bacterial viability. A high bioavailability of an iron form is usually correlated with high reactivity.

Ferric pyrophosphate is a water-insoluble iron compound which has been used to fortify food products. This form of iron has the advantage that it does not cause organoleptic changes to the food vehicle. However, in view of its lower bioavailability, preferably ferric pyrophosphate is used in the compositions of the present invention in a finely divided form. This is advantageous since finely divided forms of iron typically have an improved absorption. Additionally, in compositions of the invention which are to be reconstituted into water or other beverage, the use of an iron source in finely divided form has the further advantage of enabling the iron source to be rapidly and well-dispersed into water or other beverage due to a higher surface area.

The ferric pyrophosphate employed in any composition of the present invention may comprise microparticles. Preferably, in any aspect or embodiment of the present invention, the iron source (especially ferric pyrophosphate) has a particle size distribution $D_{90}$ of: about 200 microns or less, about 100 microns or less, about 50 microns or less, about 40 microns or less, about 30 microns or less, about 25 microns or less, about 15 microns or less, about 10 microns or less, about 5 microns or less, about 2 microns or less, about 1 microns or less, about 0.5 microns or less. Particularly the iron source (preferably ferric pyrophosphate) has a particle size distribution $D_{90}$ of about 30 microns or less, about 25 microns or less, about 15 microns or less, about 10 microns or less, about 5 microns or less, about 2 microns or less, about 1 micron or less, about 0.5 micron or less. More preferably, the iron source (preferably ferric pyrophosphate) has a particle size distribution $D_{90}$ of about 10 microns or less, about 5 microns or less, about 2 microns or less, about 1 micron or less, about 0.5 micron or less. The ferric pyrophosphate may particularly have a particle size distribution $D_{90}$ of about 1 micron or less, about 0.5 micron or less.

The iron source (preferably ferric pyrophosphate) may have a particle size distribution $D_{97}$ of: about 25 microns or less, 15 about microns or less, or about 10 microns or less, about 5 microns or less, about 2 microns or less, about 1 microns or less, or about 0.5 microns or less.

The iron source (preferably ferric pyrophosphate) may have arl average particle size of about 0.001 to about 10 microns, about 0.001 to about 5 microns, about 0.005 to about 5 microns, about 0.025 to about 5 microns, about 0.01 to about 5 microns, about 0.05 to about 5 microns, about 0.05 to about 2 microns, about 0.25 to about 1 micron, and about 0.1 to about 0.5 microns.

According to any aspect or embodiment of the present invention, the ferric pyrophosphate may be provided in the form of an emulsion or colloidal dispersion, for example, emulsified with fatty acid esters. The emulsion may comprise microparticles of ferric pyrophosphate. For example, the ferric pyrophosphate in the emulsion may have an average particle size of about 0.025 to about 5 microns, about 0.01 to about 5 microns, about 0.05 to about 5 microns, about 0.05 to about 2 microns, about 0.25 to about 1 micron, and about 0.1 to about 0.5 microns. Preferably the emulsified form of ferric pyrophosphate may have an average particle size of about 0.05 to about 2 microns, about 0.25 to about 1 micron, and about 0.1 to about 0.5 microns. More preferably, the emulsified form of ferric pyrophosphate has an average particle size of about 0.1 to about 0.5 microns or about 0.2 to about 0.4 microns. For example, a particularly suitable emulsified form of ferric pyrophosphate is commercially available under the tradename SunActive Fe® (manufactured by Taiyo Kagaku Co., Ltd., Yokkaichi, Mie, Japan) which is a ferric pyrophosphate emulsion (essentially ferric pyrophosphate coated in fats—glycerol esters of fatty acids—with emulsifiers—enzymatically hydrolysed soya lecithin, wherein the ferric pyrophosphate has a small particle size, for example, average size 0.3 micron). This form of ferric pyrophosphate advantageously has a comparable bioavailability to ferrous sulfate.

Alternatively the ferric pyrophosphate may be in a finely divided powder form, e.g. microparticulate form, having the particle size distributions as discussed herein. The ferric pyrophosphate powder may have an average particle size of about 0.025 to about 30 microns, about 0.01 to about 20 microns, about 0.05 to about 15 microns, about 0.05 to about 15 microns, about 0.25 to about 15 micron, about 0.1 to about 10 microns, about 1 to about 10 microns, or about 2 to about 10 microns. Preferably the ferric pyrophosphate powder may have an average particle size of about 0.1 to about 10 microns, about 1 to about 10 microns, or about 2 to about 10 microns. More preferably, the ferric pyrophosphate powder has an average particle size of about 1 to about 10 microns, or about 2 to about 10 microns. The ferric pyrophosphate powder may be highly dispersible in water. Microparticulate ferric pyrophosphate is commercially available from Dr. Paul Lohmann GmbH, Emmerthal, Germany (for example, a micronized powder having a $D_{50}$ of approximately 5 microns, a micronized powder having a $D_{50}$ of approximately 3 microns, a Superfine powder having a $D_{97}$ of approximately 14 microns, an Ultrafine micronized powder having $D_{97}$ of about 7 microns). Particularly the Ultrafine ferric pyrophosphate powder having a $D_{97}$ of about 7 microns may be used.

In preferred embodiments, compositions according to any aspect of the present invention may comprise ferric pyrophosphate in powder form, preferably in microparticulate form, wherein the $D_{90}$ particle size distribution can be about 25 microns or less, about 15 microns or less, about 10 microns or less, or about 5 microns or less. Alternatively the ferric pyrophosphate in powder form may have $D_{97}$ particle size distribution of about 15 microns or less, about 10 microns or less, or about 5 microns or less, and particularly about 10 microns or less.

We have found that despite their small particle size and therefore expected higher reactivity, the finely divided, for example microparticulate, forms of ferric pyrophosphate which are preferably employed in the compositions of the present invention, surprisingly do not result in a loss of pro biotic bacteria viability.

Preferably, a dosage form according to the present invention can provide a daily dose of iron in an amount corresponding to the Dietary Reference Intake (DRI) of iron for the particular individual for whom the dose is intended. By way of example, the dose can provide 1-100 milligrams of iron. However, a clinician can prescribe a dose comprising a greater amount of iron for ingestion under medical supervision.

In any aspect or embodiment of the present invention, the composition may be a dosage form in the form of a maternal supplement, which may be administered to a pregnant and/or lactating female. In this case, the dosage form may contain from about 5 to about 100 mg, about 5 to about 75 mg, about 5 to about 50 mg, about 10 to about 40 mg, or about 10 to about 30 mg of iron per day. For lactating mothers, the dosage form may contain from about 5 to about 50 mg, about 5 to about 30 mg, or about 5 to about 20 mg, about 5 to about 15 mg of iron per day. The dose can be provided, for example, as one, two, or more unit dosage forms (e.g. tablets, capsules, lozenges, powders, sachets, etc.).

Compositions and Administration

The compositions of the present invention may contain additional vitamins, minerals, and micronutrients, including trace elements, in accordance with the recommendations (e.g. recommended daily intake guidelines) of government bodies.

For example, the compositions of any embodiment of the present invention can include trace elements that are particularly beneficial for the pregnant/lactating female and the fetus, such as zinc, manganese, magnesium (which acts as an anti-stress agent and reduces the occurrence of cramp), iodine (essential in the production of thyroid hormones), copper (which assists with iron absorption and thus additionally has an anti-anemic effect, and also has a role in the maintenance of bones and cartilage), iodine, selenium (an antioxidant which intervenes in the metabolism of free radicals and other substances produced by the oxidation of lipids in cell membranes), chromium (which has an important role in carbohydrate metabolism and insulin regulation, and molybdenum).

Further, the compositions of any aspect or embodiment of the present invention may include vitamins such as A, B, C, D, E and/or their precursors and their mixtures. Said composition preferably comprises said vitamins chosen from the group comprising myo-inositol, β-carotene, vitamin B1, vitamin B2, vitamin B3, vitamin B4, vitamin B5, vitamin B6, vitamin B12, folic acid, vitamin C (ascorbic acid or ascorbate), vitamin D3, vitamin E, biotin and mixtures thereof. In particular, folic acid promotes the proper development of the embryo and significantly reduces the occurrence of disease in the newborn (e.g. neural tube defects). Vitamin D is known to help in the formation of the skeleton of the newborn, while vitamin A is important for growth. Preferably the vitamin A is administered as pro-vitamin A or β-carotene, which is a non-toxic source from which the body can manufacture vitamin A as required. Vitamin C (in the form of ascorbic acid or ascorbate) is known to strengthen the placenta and the general condition of the pregnant woman and promotes the absorption of iron—the latter is particularly advantageous for the compositions of the present invention that are for treating or preventing iron deficiency and/or anemia.

The composition particularly may comprise at least one of Vitamin C (ascorbic acid or ascorbate) and/or copper, in order to aid iron absorption. The composition may comprise calcium, magnesium, phosphorus, zinc, copper, iodine, selenium, beta carotene, Vitamin C, Vitamin B1, Vitamin B6, Vitamin B2, niacin, Vitamin B12, folic acid, biotin, Vitamin D, Vitamin E.

For example, the composition may provide a daily dose one or more of the following micronutrients in the ranges given: 300 to 500 mg calcium, 50 to 100 mg magnesium, 150 to 250 mg phosphorus, 1 to 7 mg zinc, 0.1 to 0.3 mg copper, 50 to 200 g iodine, 5 to 15 g selenium, 1000 to 3000 g beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 g Vitamin B12, 100 to 800 g folic acid, 30 to 70 g biotin, 1 to 5 g Vitamin D, 3 to 10 IU Vitamin E For example, the composition may provide a daily dose one or more of the following micronutrients in the ranges given: 100 μg to 500 mg calcium, 50 to 100 mg magnesium, 150 to 250 mg phosphorus, 1 to 40 mg zinc, 0.1 to 0.3 mg copper, 22 μg to 200 g iodine, 5 to 15 g selenium, 720 μg to 3000 g beta carotene, 10 to 80 mg Vitamin C, 1 to 2 mg Vitamin B1, 0.5 to 3 mg Vitamin B6, 0.5 to 3 mg Vitamin B2, 5 to 18 mg niacin, 5 μg to 2.0 g Vitamin B12, 400 μg to 800 g folic acid, 30 to 70 g biotin, 10 μg to 5 g Vitamin D, 3 to 10 IU Vitamin E, myo-inositol.

For example, a composition according to any aspect or embodiment of the present invention may provide a daily dose of myo-inositol (1-8 g), Vitamin D (5-30 μg), Vitamin B6 (1-10 mg), Vitamin B12 (1-20 μg), Vitamin B2 (1-5 mg), Zinc (1-30 mg), β-carotene (200-1500 μg), Folic acid (200-600 μg), Iron (5-25 μg), Calcium (50-300 μg) and Iodine (50-250 μg).

A composition according to the invention may be a dairy product such as an acidified dairy product, for example a spoonable or drinkable yoghurt.

A composition according to any aspect or embodiment of the present invention may be in form of a supplement for administration to a female who is planning to become pregnant. Thus the supplement may be administered prior to conception, i.e. as a pre-pregnancy supplement. The pre-pregnancy supplement may, for example, be administered at least one month prior to conception. Particularly the pre-pregnancy supplement may be administered at least 2, at least 3, at least 4, at least 6 at least 9 or at least 12 months prior to conception. Alternatively, or additionally, compositions according to any aspect or embodiment of the present invention may be in the form of a supplement for administration to a pregnant female at any stage of pregnancy (pregnancy supplement) or to the mother after birth and/or during lactation (lactation supplement) as a supplement. Particularly the pregnancy supplement may be administered for at least 1, at least 2, at least 3, at least 4, at least 6, at least 8, at least 9, or throughout the duration of the pregnancy. Particularly, the lactation supplement may be administered at the start of lactation for at least 1, at least 2, at least 3, at least 4, at least 6, or throughout the duration of lactation. The supplement may be in any suitable form for oral administration. Particularly the supplement may be in the form of a tablet, capsule or powder.

Preferably compositions of any aspect or embodiment of the present invention are administered at least one month prior to conception, as a pre-pregnancy supplement.

Preferably the composition is administered during at least the second and/or third trimester of pregnancy. More preferably, the composition is administered to the pregnant woman throughout pregnancy (i.e. for the full duration of pregnancy).

Compositions according to the present invention are preferably in a solid form The composition may, for example, be in the form of a chewable tablet, dispersible tablet, capsule, lozenge, pastille, chewing gum, powder (e.g. in a sachet), stickpack sachets, or bottle with powder in the cap. Preferably the composition is in the form of a tablet, capsule or powder. The tablet or capsule may be provided as a unit dosage form for, e.g. once or twice daily, preferably once daily, administration. A powder composition may be contained in a sachet. A powder composition according to the present invention may be used to sprinkle onto a food or beverage. A particularly preferred embodiment provides a composition according to the invention in the form of a sachet containing a powder, wherein the powder can be dispersed into a beverage (e.g. water, fruit juice, milk, etc.) to provide a palatable nutrient liquid for oral administration.

Alternatively, the composition may be in the form of a therapeutic nutritional composition. The composition may be a nutritionally complete formula, for example including a source of protein, carbohydrate and fat.

A nutritionally complete formula for administration to pregnant women according to the invention may comprise a source of protein. Any suitable dietary protein may be used for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. The composition may also contain a source of carbohydrates and a source of fat. The source of fat may comprise at least one omega-3 polyunsaturated fatty acid, for example those found in fish oils, especially eicosapentaenoic acid (EPA), and docosahexaenoic acid (DHA).

If the formula includes a fat source in addition to the omega-3 polyunsaturated fatty acid(s), the fat source preferably provides 5% to 40% of the energy of the formula; for example 20% to 30% of the energy. A suitable fat profile may be obtained using a blend of canola oil, corn oil and high-oleic acid sunflower oil.

A source of carbohydrate may be added to the composition. It preferably provides 40% to 80% of the energy of the formula. Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum arabic, fructooligosaccharides, galacto-oligosaccharides, sialyl-lactose and oligosaccharides derived from animal milks. A preferred fibre blend is a mixture of galacto-oligosaccharides with short chain fructo-oligosaccharides. Preferably, if fibre is present, the fibre content is between 2 and 40 g/l of the formula as consumed, more preferably between 4 and 10 g/l.

The composition may be in the form of a tablet, capsule, powder, sachet or lozenge. Preferably the composition is in the form of a powder.

Compositions according to the present invention may further comprise at least one pharmaceutically acceptable additive or excipient, for example selected from stabilizers, fillers, emulsifiers, surfactants, solubilising agents, adsorbents, flowing agents, stabilizers, buffers, lubricants, wetting agents, carriers, antioxidants, thickeners, anticaking agents, coating agents, taste masking agents, antioxidants, preservatives, flavouring agents and dyes.

A solid composition according to the present invention may be prepared in any suitable manner. For example, it may be prepared by blending together the protein, the carbohydrate source, and the fat source (if these are to be included) in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MP a to about 30 MPa in the first stage and about 2 MPa to about 10 MP a in the second stage. The homogenised mixture may then be further cooled to add any heat sensitive components; such as vitamins and minerals. The pH and solids content of the homogenised mixture are conveniently adjusted at this point. The homogenised mixture is transferred to a suitable drying apparatus such as a spray dryer or freeze dryer and converted to powder. The powder should have a moisture content of less than about 5% by weight. The pro biotic bacteria may then be added to this powder.

The selected pro biotic bacteria may be cultured according to any suitable method and prepared for addition to the composition by freeze-drying or spray-drying, for example. Alternatively, bacterial preparations can be bought from specialist suppliers such as Christian Hansen and Valio already prepared in a suitable form for addition to food products and supplements. The pro biotic bacteria may be added to the formula in an amount of: 10e3 to 10e 14 cfu/g powder, preferably 10e4 to 10e12 cfu/g powder, more preferably 10e5 to 10e12 and most preferably between 10e7 and 10e 12 cfu/g powder.

The powder may be packaged in a sachet, for example as a powder for addition to a beverage. For reconstitution, the powder may be stirred into a suitable beverage, e.g. water, fruit juice, milk, etc., typically at room temperature, for consumption.

The invention will now be further illustrated by reference to the following examples.

EXAMPLES

Example 1

In the example below, we consider one sachet of powder containing 6 mg of iron and 333.3 mg of probiotic bacteria preblend (i.e. a mix of dried *Lactobacillus rhamnosus* (*L. rhamnosus* GG1) and *Bifidobacterium lactis* (*B. lactis* BB12) in a maltodextin carrier at a concentration of around 1.0E+10 cfu per gram of powder). For practical reasons (accuracy in weighed amount), the amounts have been multiplied by 5.

Five preparations containing various iron fortifying agents and probiotic bacteria, and a control composition containing pro biotic bacteria and no iron fortifying agent were tested, as follows:

|  | Preparation | | | | | |
| --- | --- | --- | --- | --- | --- | --- |
|  | 1 | 2 | 3 | 4 | 5 | 6 |
| Iron type | Ferrous Bisglycinate powder | Ferric Pyrophosphate Emulsion (Essentially ferric pyrophosphate coated in fat) | Micronized ferric pyrophosphate powder | Non-micronized ferric pyrophosphate powder | Ferric ammonium citrate powder (non-micronized) | Control with probiotic bacteria preblend |
| Product/Supplier | Albion | SunActive Taiyo | Ultrafine P. Lohmann | P. Lohmann | P. Lohmann | NA |
| Purity (% Fe) | 29 wt % | 8 wt % | 25 wt % | 25 wt % | 14.5 wt % | NA |
| Reactive form | +2 form | +3 form | +3 form | +3 form | +3 form | NA |
| Amount of iron salt (mg) | 159.9 | 375.9 | 129.9 | 129.9 | 296.9 | 9 |
| Amount of pro biotic | 1666.59 | 1666.59 | 1666.59 | 1666.59 | 1666.59 | 1666.59 |

-continued

|  | Preparation | | | | | |
| --- | --- | --- | --- | --- | --- | --- |
|  | 1 | 2 | 3 | 4 | 5 | 6 |
| bacteria preblend (mg) | | | | | | |
| Amount of diluent TS+ (in g) | 998.2 | 998.9 | 998.2 | 998.2 | 998.1 | 998.3 |

For each preparation, the required amount of iron fortificant was weighed. The iron fortificant was mixed with the specified amount of diluent TS+, i.e., a reconstitution solution with Tryptone, Sodium Chloride and Antifoam at 37° C. having the following composition:

| Tryptone | 15 g |
| --- | --- |
| Sodium chloride | 8.5 g |
| Antifoam | 1 mL of a 10% solution in water |
| Distilled water | up to 1000 mL |
| pH | 7.0 ± 0.2 (at 25° C.) |

The TS+ is prepared by the following process:
Dissolve the components in the water by warming gently
Adjust the pH if necessary
Sterilize by heat treatment at 121° C. for 15 minutes
Storage conditions: 4° C.±2° C. for 4 weeks.
TS+ may also be obtained commercially.
The mixture was agitated until complete homogenization of the solution (3 min).
The probiotic bacteria preblend (PP036) was added and the mixture agitated for 1 min.
Each of the six preparations were analysed in triplicate.
Bacterial viability was determined immediately after preparation by plating of serial dilutions and subsequent counting of colony forming units. Any suitable method of measuring bacterial viability can be used [e.g. Jett, B. D. et al, "Simplified agar plate method for quantifying viable bacteria"—Biotechniques (1997), 23, 648-650; Sieuwerts, S., et al., "A simple and fast method for determining colony forming units"—Letters in Applied Microbiology (2008), 47, 275-278)]. The principle of the method is the following:
Samples containing probiotics are weighed, rehydrated in a diluent (TS+) and homogenized by stomaching.
Serial decimal dilutions are performed in the same diluent (TS+)
1 mL of each appropriate dilution is transferred to Petri dishes and mixed with a specific agar (pour-plate method)
The inoculated solidified agar plates are incubated under specific conditions enabling colony formation by the target bacteria (selective enumeration)
Colonies are counted and results are calculated and expressed in colony forming units per gram of sample (CFU/g).

The following results were obtained:

|  | Preparation | | | | | |
| --- | --- | --- | --- | --- | --- | --- |
|  | 1 | 2 | 3 | 4 | 5 | 6 |
| Iron [mg] | 60.2 | 150.3 | 47.9 | 48.1 | 82.9 | 0 |
| Probiotic preblend [mg] | 666.4 | 666.1 | 666.3 | 666 | 665.9 | 665.9 |
| Diluent [ml] TS+ | 399.83 | 399.87 | 400.04 | 399.69 | 399.9 | 399.91 |
| Selected dilution for numeration | 5 | 5 | 5 | 5 | 5 | 5 |
| Duplicate   a | 182 | 271 | 224 | 315 | 173 | 272 |
|           b | 171 | 249 | 262 | 265 | 162 | 243 |
|           c | 208 | 297 | 226 | 292 | 163 | 256 |
| CFU/mL in the reconstituted product | 1.87E+07 | 2.72E+07 | 2.37E+07 | 2.91E+07 | 1.66E+07 | 2.57E+07 |
| CFU/sachet | 3.74E+09 | 5.44E+09 | 4.75E+09 | 5.81E+09 | 3.32E+09 | 5.14E+09 |
| Log | 9.57 | 9.74 | 9.68 | 9.76 | 9.52 | 9.71 |
| Log loss during reconstitution | −0.14 | 0.03 | −0.03 | 0.05 | −0.19 | 0.00 |

CPU/Sachet=CPU content in the initial 333 mg of the pro biotic bacteria Preblend Log=CPU/sachet expressed as a log value Log loss during reconstitution=cfu of the reference in log–cfu of the tested sample in log (negative numbers indicate a loss)

Standard deviation for each result is about 0.04. The above results show that Preparations 2, 3 and 4, containing ferric pyrophosphate have a similar log loss value, indicating that these iron fortifying agents do not cause loss of bacterial viability compared to compositions containing ferrous bisglycinate (Preparation 1) and ferric ammonium citrate (Preparation 5). This result is particularly surprising in view of the fact that ferrous bisglycinate is more water soluble than ferric pyrophosphate and hence very reactive, and ferric ammonium citrate contains iron in the same oxidation state as ferric pyrophosphate. Moreover, the ferric pyrophosphate in Preparation 2 and Preparation 3 are in a finely divided form (i.e. comprising microparticles), which increases the exposure of the bacteria to the iron due to greater surface area, and hence would be expected to result in a higher viability loss.

Example 2

A powder formulation comprising *L. rhamnosus* (and optionally *B. lactis*) and ferric pyrophosphate may be prepared. The formulation may be dispersed into water or other beverage to provide a nutritional supplement as follows:

|  | Per 100 g | Per 100 kcal Ready to drink | Per serving (190 ml) |
|---|---|---|---|
| Energy (kcal) | 100 | 65 | 130 |
| *L. rhamnosus* GG1 |  |  | 10e10 |
| *B. lactis* BB12 |  |  | 10e10 |
| Ferric pyrophosphate (mg equivalent iron) | 12 | 7.5 | 15 |
| Fat (g) | 0.92 | 0.60 | 1.20 |
| Protein (g) | 3.54 | 2.30 | 4.60 |
| Carbohydrate (g) | 19.4 | 12.60 | 25.2 |
| Dietary fibre (g) | 3.62 | 2.35 | 4.70 |
| Minerals |  |  |  |
| Sodium (mg) | 51 | 33 | 66 |
| Potassium (mg) | 238 | 155 | 310 |
| Chloride (mg) | 123 | 80 | 160 |
| Calcium (mg) | 308 | 200 | 400 |
| Phosphorus (mg) | 162 | 105 | 210 |
| Magnesium (mg) | 58.0 | 38 | 76 |
| Selenium (µg) | 7.7 | 5.0 | 10.0 |
| Vitamins |  |  |  |
| Beta carotene (µg) | 1600 | 1050 | 2100 |
| Vitamin D (µg) | 3.8 | 2.50 | 5.0 |
| Vitamin E (IU) | 4.6 | 3.0 | 6.0 |
| Vitamin C (mg) | 38 | 25 | 50 |
| Vitamin B1 (mg) | 1.2 | 0.75 | 1.5 |
| Vitamin B2 (mg) | 1.3 | 0.85 | 1.7 |
| Niacin (mg) | 12 | 8 | 16 |
| Vitamin B6 (mg) | 1.1 | 0.7 | 1.4 |
| Folic acid (µg) | 310 | 200 | 400 |
| Vitamin B12 (µg) | 1.2 | 0.75 | 1.5 |
| Biotin (µg) | 54 | 35 | 70 |
| Other Trace Elements |  |  |  |
| Iodine (µg) | 150 | 100 | 200 |
| Copper (mg) | 0.20 | 0.13 | 0.26 |
| Zinc (mg) | 3.8 | 2.5 | 5.0 |

Example 3

A powder formulation comprising *L. Rhamnosus* (and optionally *B. lactis*) and ferric pyrophosphate may be prepared. The formulation may be dispersed into water or other beverage to provide a nutritional supplement as follows:

| Ingredient | Amount per daily dose |
|---|---|
| Myo-inositol | 4 g |
| Vitamin D | 10 µg |
| Vitamin B6 | 2.6 mg |
| Vitamin B12 | 5.2 µg |
| Vitamin B2 | 1.8 mg |
| Zinc | 10 mg |
| P-carotene | 720 µg |
| Folic acid | 400 µg |
| Ferric pyrophosphate (µg equivalent Iron) | 12 µg |
| Calcium | 150 µg |
| Iodine | 150 µg |
| *Lactobacillus rhamnosus* GG[1] | 1 × 10⁹ cfu |
| *Bifidobacterium lactis* BB1[2] | 1 × 10⁹ cfu |

[1] Strain deposited as CGMCC 1.3724
[2] Strain deposited as CNCM I-3446

The composition may be administered to a woman desiring to get pregnant during at least one month prior to pregnancy and later to the same woman for at least one month during pregnancy.

Further aspects and embodiments of the present invention are set out in the following numbered paragraphs 1. An oral composition comprising:
    at least one probiotic bacteria selected from the genera: *Lactobacillus*, *Bifidobacterium*, and *Bacillus*, and ferric pyrophosphate.
2. A composition according to paragraph 1 wherein the ferric pyrophosphate is microparticulate.
3. A composition according to paragraph 1 or paragraph 2 wherein the ferric pyrophosphate is micronized.
4. A composition according to any of paragraphs 1-3 wherein the ferric pyrophosphate is in the form of an emulsion with at least one fatty acid ester.
5. A composition according to any of paragraphs 1-4, wherein the ferric pyrophosphate has a particle size distribution $D_{90}$ of: 200 microns or less, 100 microns or less, 50 microns or less, 40 microns or less, 30 microns or less, 25 microns or less, 15 microns or less, 10 microns or less or 5 microns or less.
6. A composition according to any of paragraphs 1-4, wherein the ferric pyrophosphate has a particle size distribution $D_{90}$ of: 30 microns or less, 25 microns or less, 15 microns or less, 10 microns or less or 5 microns or less.
7. A composition according to any of paragraphs 1-4, wherein the ferric pyrophosphate has a particle size distribution $D_{90}$ of: 25 microns or less, 15 microns or less, 10 microns or less or 5 microns or less.
8. A composition according to any of paragraphs 1-4, wherein the ferric pyrophosphate has a particle size distribution $D_{90}$ of: 10 microns or less or 5 microns or less.
9. A composition according to any of paragraphs 1-4, wherein the ferric pyrophosphate has a particle size distribution $D_{97}$ of: 25 microns or less, 15 microns or less, 10 microns or less or 5 microns or less, about 2 microns or less, about 1 microns or less, or about 0.5 microns or less, preferably wherein the ferric pyrophosphate has a particle size distribution $D_{97}$ of: 10 microns or less or 5 microns or less.
10. A composition according to any of paragraphs 1-4, wherein the ferric pyrophosphate has a particle size distribution $D_{90}$ of: less than 1 micron, or less than 0.5 micron: preferably wherein the ferric pyrophosphate has a particle size distribution $D_{90}$ of: less than 0.5 micron.
11. A composition according to any of paragraphs 1-10, wherein the ferric pyrophosphate has an average particle size of about 0.001 to about 10 microns, about 0.001 to about 5 microns, about 0.005 to about 5 microns, about 0.025 to about 5 microns, about 0.01 to about 5 microns, about 0.05 to about 5 microns, about 0.05 to about 2 microns, about 0.25 to about 1 micron, and about 0.1 to about 0.5 microns 12. A composition according to any of paragraphs 1-4, wherein the ferric pyrophosphate is in the form of an emulsion with at least one fatty acid ester, wherein the ferric pyrophosphate in the emulsion has an average particle size of about 0.025 to about 5 microns, about 0.01 to about 5 microns, about 0.05 to about 5 microns, about 0.05 to about 2 microns, about 0.25 to about 1 micron, or about 0.1 to about 0.5 microns; preferably wherein the ferric pyrophosphate in the emulsion has an average particle size of about 0.05 to about 2 microns, about 0.25 to about 1 micron, or about 0.1 to about 0.5 microns; and more preferably wherein the ferric pyrophosphate in the emulsion has an average particle size of about 0.1 to about 0.5 microns or about 0.2 to about 0.4 microns.

13. A composition according to any of paragraphs 1-3 wherein the ferric pyrophosphate is in the form of a powder comprising microparticles wherein the ferric pyrophosphate powder preferably has an n average particle size of about 0.025 to about 30 microns, about 0.01 to about 20 microns, about 0.05 to about 15 microns, about 0.05 to about 15 microns, about 0.25 to about 15 micron, about 0.1 to about 10 microns, about 1 to about 10 microns, or about 2 to about 10 microns; preferably wherein the ferric pyrophosphate powder has an average particle size of about 0.1 to about 10 microns, about 1 to about 10 microns, or about 2 to about 10 microns; and more preferably wherein the ferric pyrophosphate powder has an average particle size of about 1 to about 10 microns, or about 2 to about 10 microns.

14. A composition according to any of paragraphs 1-13, wherein the probiotic bacteria comprises a *Lactobacillus*.

15. A composition according to any preceding paragraph wherein the probiotic bacteria comprises a species selected from the group consisting of: *L. acidophilus, L. casei, L. paracasei, L. rhamnosus, L. delbrueckii* subsp. *bulgaricus, L. brevis, L. johnsonii, L. plantarum* and *L. fermentum, L. casei* Shirota and *L. casei rhamnosus*.

16. A composition according to any preceding paragraph wherein the probiotic bacteria comprises an *L. rhamnosus* strain.

17. A composition according to any preceding paragraph wherein the *L. rhamnosus* strain is selected from the group consisting of: *L. rhamnosus* CRL 1505, *L. rhamnosus* GG, *L. rhamnosus* CGMCC 1.3724 or *L. rhamnosus* NCC 4007.

18. A composition according to any preceding paragraph wherein the probiotic bacteria comprises *L. rhamnosus* CGMCC 1.3724.

19. A composition according to any preceding paragraph wherein the probiotic bacteria comprises a *Bifidobacterium*.

20. A composition according to any preceding paragraph wherein the pro biotic bacteria comprises a species selected from the group consisting of: *B. lactis, B. longum, B. breve, B. infantis, B. adolescentis, B. animalis,* and *B. bifidum*.

21. A composition according to any preceding paragraph the probiotic bacteria is selected from the group consisting of: *B. lactis, B. longum,* preferably *B. longum* ATCC BAA-99, *B. longum* B8536, *B. longum* AH1206, *B. breve* AH1205 and *B. infantis* 35624, and most preferably *B. lactis* and *B. breve*.

22. A composition according to any preceding paragraph the probiotic bacteria comprises a *Bacillus*.

23. A composition according to any preceding paragraph wherein the probiotic bacteria comprises a species selected from the group consisting of: *B. subtilis, B. coagulans, B. subtilis, B. clausii,* B, *pumilus,* and *B. cereus*.

24. A composition according to any preceding paragraph wherein the probiotic bacteria comprises a *B. cereus* strain.

25. A composition according to any preceding paragraph wherein the probiotic bacteria strain is selected from the group consisting of *B. cereus* NVH 75/95 or *B. cereus* IP 5832.

26. A composition according to any of paragraphs 1-21, wherein the probiotic bacteria comprises a mixture of *L. rhamnosus* (preferably *L. rhamnosus* GG1/*L. rhamnosus* CGMCC 1.3724) and *B. lactis* (preferably *B. lactis* BB12 *B. lactis* CNCM I-3446).

27. A composition according to paragraph 1 comprising a *Lactobacillus* probiotic bacteria, and ferric pyrophosphate.

28. A composition according to paragraph 27 comprising a *L. rhamnosus* strain.

29. A composition according to paragraph 28, comprising a *L. rhamnosus* strain selected from the group consisting of: *L. rhamnosus* CRL1505, *L. rhamnosus* GG, *L. rhamnosus* CGMCC 1.3724 and *L. rhamnosus* NCC 4007, and preferably *L. rhamnosus* CGMCC 1.3724.

30. A composition according to any of paragraphs 27-29, wherein the pro biotic bacteria comprises a mixture of *L. rhamnosus* (preferably *L. rhamnosus* GG1 *L. rhamnosus* CGMCC 1.3724) and *B. lactis* (preferably *B. lactis* BB12 *B. lactis* CNCM I-3446).

31. A composition according to any of paragraphs 27-30, wherein the ferric pyrophosphate is microparticulate, and/or is in the form of an emulsion with a fatty acid ester.

32. A composition according to any of paragraphs 27-31 wherein the ferric pyrophosphate has a particle size distribution as defined in any of paragraphs 5-11.

33. A composition according to any of paragraphs 27-31, wherein the ferric pyrophosphate is in the form of an emulsion with at least one fatty acid ester, and wherein the ferric pyrophosphate in the emulsion has an average particle size of about 0.025 to about 5 microns, about 0.01 to about 5 microns, about 0.05 to about 5 microns, about 0.05 to about 2 microns, about 0.25 to about 1 micron, or about 0.1 to about 0.5 microns; preferably wherein the ferric pyrophosphate in the emulsion has an average particle size of about 0.05 to about 2 microns, about 0.25 to about 1 micron, or about 0.1 to about 0.5 microns; and more preferably wherein the ferric pyrophosphate in the emulsion has an average particle size of about 0.1 to about 0.5 microns or about 0.2 to about 0.4 microns.

34. A composition according to any of paragraphs 22-31 wherein the ferric pyrophosphate is in the form of a powder comprising microparticles wherein the ferric pyrophosphate powder preferably has an n average particle size of about 0.025 to about 30 microns, about 0.01 to about 20 microns, about 0.05 to about 15 microns, about 0.05 to about 15 microns, about 0.25 to about 15 micron, about 0.1 to about 10 microns, about 1 to about 10 microns, or about 2 to about 10 microns; preferably wherein the ferric pyrophosphate powder has an average particle size of about 0.1 to about 10 microns, about 1 to about 10 microns, or about 2 to about 10 microns; and more preferably wherein the ferric pyrophosphate powder has an average particle size of about 1 to about 10 microns, or about 2 to about 10 microns.
35. A composition according to paragraph 1 comprising *L. rhamnosus*, and more preferably, *L. rhamnosus* CGMCC 1.3724; and ferric pyrophosphate, wherein the ferric pyrophosphate is microparticulate and/or is in the form of an emulsion with a fatty acid ester.
36. A composition according to paragraph 35, comprising a mixture of *L. rhamnosus* (preferably *L. rhamnosus* GG1/*L. rhamnosus* CGMCC 1.3724) and *B. lactis* (preferably *B. lactis* BB12/*B. lactis* CNCM I-3446).
37. A composition according to any of paragraphs 35-36, wherein the ferric pyrophosphate has a particle size distribution $D_{90}$ of: 40 microns or less, 30 microns or less, 25 microns or less, 15 microns or less, 10 microns or less, 5 microns or less, 2 microns or less, 1 micron or less, or 0.5 microns or less.
38. A composition according to paragraph 37, wherein the ferric pyrophosphate has a particle size distribution $D_{90}$ of: 25 microns or less, 10 microns or less, 5 microns or less, 2 microns or less, 1 micron or less, or 0.5 microns or less, preferably wherein the ferric pyrophosphate has a particle size distribution $D_{90}$ of: 10 microns or less; 5 microns or less.
39. A composition according to paragraph 37, wherein the ferric pyrophosphate has a particle size distribution $D_{90}$ of: 2 microns or less, or 1 micron or less.
40. A composition according to paragraph 37, wherein the ferric pyrophosphate has a particle size distribution of 0.5 microns or less.
41. A composition according to paragraph 37, wherein the ferric pyrophosphate has an average particle size of about 0.001 to about 10 microns, about 0.001 to about 5 microns, about 0.005 to about 5 microns, about 0.025 to about 5 microns, about 0.01 to about 5 microns, about 0.05 to about 5 microns, about 0.05 to about 2 microns, about 0.25 to about 1 micron, and about 0.1 to about 0.5 microns.
42. A composition according to any of paragraphs 35-36, wherein the ferric pyrophosphate is in the form of an emulsion with at least one fatty acid ester, and wherein the ferric pyrophosphate in the emulsion has an average particle size of about 0.025 to about 5 microns, about 0.01 to about 5 microns, about 0.05 to about 5 microns, about 0.05 to about 2 microns, about 0.25 to about 1 micron, or about 0.1 to about 0.5 microns: preferably wherein the ferric pyrophosphate in the emulsion has an average particle size of about 0.05 to about 2 microns, about 0.25 to about 1 micron, or about 0.1 to about 0.5 microns; and more preferably wherein the ferric pyrophosphate in the emulsion has an average particle size of about 0.1 to about 0.5 microns or about 0.2 to about 0.4 microns.
43. A composition according to any of paragraphs 35-36, wherein the ferric pyrophosphate is in the form of a powder comprising microparticles of ferric pyrophosphate wherein the ferric pyrophosphate powder preferably has an n average particle size of about 0.025 to about 30 microns, about 0.01 to about 20 microns, about 0.05 to about 15 microns, about 0.05 to about 15 microns, about 0.25 to about 5 micron, about 0.1 to about 10 microns, about 1 to about 10 microns, or about 2 to about 10 microns; preferably wherein the ferric pyrophosphate powder has an average particle size of about 0.1 to about 10 microns, about 1 to about 10 microns, or about 2 to about 10 microns; and more preferably wherein the ferric pyrophosphate powder has an average particle size of about 1 to about 10 microns, or about 2 to about 10 microns.
44. A composition according to any of paragraphs 1-43, further comprising one or more micronutrients, preferably selected from the group consisting of vitamins, minerals and trace elements.
45. A composition according to any of paragraphs 1-44 in the form of a dietary supplement, and preferably in the form of a pre-pregnancy (pre-conception) supplement and/or maternal supplement (i.e. pregnancy and/or lactation supplement).
46. A composition according to any of paragraphs 1-45 wherein the composition is solid.
47. A composition according to any of paragraphs 1-46 wherein the composition is a solid dosage form, preferably selected from the group consisting of a tablet, chewable tablet, a dispersible tablet, capsule, powder, sachet containing a powder, stickpack sachet, bottle with powder in a cap, pastille, chewing gum or lozenge.
48. A composition according to any of paragraphs 1-47 wherein the composition is a powder, preferably wherein the powder is for dispersion into a beverage.
49. A composition according to any of paragraphs 1-48 for use in: the treatment or prevention of gestational diabetes, the treatment or prevention of iron deficiency and/or the treatment or prevention of anemia in a pregnant or lactating female subject, or for the treatment or prevention of iron deficiency and/or treatment or prevention of anemia in a female subject pre-pregnancy (i.e. prior to conception).
50. A composition according to any of paragraphs 1-49 for use as an iron supplement pre-pregnancy, during pregnancy and/or during lactation.
51. A composition according to any of paragraphs 1-50 for use as a pro biotic pre-pregnancy (i.e. pre-conception), pregnancy and/or lactation supplement.
52 Use of ferric pyrophosphate as a fortifying agent in an oral probiotic supplement, comprising at least one probiotic bacteria.
53. Use according to paragraph 52 wherein the probiotic bacteria comprises at least one of the genera: *Lactobacillus, Bifidobacterium*, and *Bacillus*.
54. Use according to paragraph 52 or paragraph 53 wherein the probiotic bacteria comprises a *Lactobacillus* species.
55. Use according to paragraph 54 wherein the *Lactobacillus* is *L. rhamnosus*, preferably a strain selected rom the group consisting of: *L. rhamnosus* CRL1505, *L. rhamnosus* GG, *L. rhamnosus* CGMCC 1.3724 or *L. rhamnosus* NCC 4007, and most preferably *L. rhamnosus* CGMCC 1.3724.
56. Use according to any of paragraphs 52-55, wherein the probiotic bacteria comprises a mixture of *L. rhamnosus* (preferably *L. rhamnosus* GG1 *L. rhamnosus* CGMCC 1.3724) and *B. lactis* (preferably *B. lactis* BB12 *B. lactis* CNCM I-3446).
57. Use according to any of paragraphs 52-56, wherein the ferric pyrophosphate is microparticulate.
58. Use according to any of paragraphs 52-57 wherein the ferric pyrophosphate has a particle size distribution as defined in any of paragraphs 5-11.
59. Use according to any of paragraphs 52-57, wherein the ferric pyrophosphate is in the form of an emulsion with at least one fatty acid ester, and wherein the ferric pyrophosphate in the emulsion has an average particle size of about 0.025 to about 5 microns, about 0.01 to about 5 microns, about 0.05 to about 5 microns, about 0.05 to about 2 microns, about 0.25 to about 1 micron, or about 0.1 to about 0.5 microns; preferably wherein the ferric pyrophosphate in the emulsion has an average particle size of about 0.05 to about 2 microns, about 0.25 to about 1 micron, or about 0.1 to about 0.5 microns; and more preferably wherein the ferric pyrophosphate in the emulsion has an average particle size of about 0.1 to about 0.5 microns or about 0.2 to about 0.4 microns.

60. Use according to any of paragraphs 52-57, wherein the ferric pyrophosphate is in the form of a powder comprising microparticles of ferric pyrophosphate wherein the ferric pyrophosphate powder preferably has an average particle size of about 0.025 to about 30 microns, about 0.01 to about 20 microns, about 0.05 to about 15 microns, about 0.05 to about 15 microns, about 0.25 to about 15 micron, about 0.1 to about 10 microns, about 1 to about 10 microns, or about 2 to about 10 microns; preferably wherein the ferric pyrophosphate powder has an average particle size of about 0.1 to about 10 microns, about 1 to about 10 microns, or about 2 to about 10 microns; and more preferably wherein the ferric pyrophosphate powder has an average particle size of about 1 to about 10 microns, or about 2 to about 10 microns.

61. Use of ferric pyrophosphate for preserving the viability of pro biotic bacteria in an oral pro biotic composition.

62. Use according to paragraph 61 wherein the probiotic bacteria comprises at least one of the genera: *Lactobacillus, Bifidobacterium*, and *Bacillus*.

63. Use according to any of paragraphs 61-62, wherein the probiotic bacteria comprises a *Lactobacillus* species.

64. Use according to paragraph 63, wherein the *Lactobacillus* is *L. rhamnosus*, preferably a strain selected rom the group consisting of: *L. rhamnosus* CRL1505, *L. rhamnosus* GG, *L. rhamnosus* CGMCC 1.3724 or *L. rhamnosus* NCC 4007, and most preferably *L. rhamnosus* CGMCC 1.3724.

65. Use according to any of paragraphs 61-64 wherein the probiotic bacteria comprises a mixture of *L. rhamnosus* (preferably *L. rhamnosus* GG1 *L. rhamnosus* CGMCC 1.3724) and *B. lactis* (preferably *B. lactis* BB12 *B. lactis* CNCM I-3446).

66. Use according to any of paragraphs 61-65, wherein the ferric pyrophosphate is microparticulate.

67. Use according to any of paragraphs 61-66 wherein the ferric pyrophosphate has a particle size distribution as defined in any of paragraphs 5-11.

68. Use according to any of paragraphs 61-66, wherein the ferric pyrophosphate is in the form of an emulsion with at least one fatty acid ester, and wherein the ferric pyrophosphate in the emulsion has an average particle size of about 0.025 to about 5 microns, about 0.01 to about 5 microns, about 0.05 to about 5 microns, about 0.05 to about 2 microns, about 0.25 to about 1 micron, or about 0.1 to about 0.5 microns; preferably wherein the ferric pyrophosphate in the emulsion has an average particle size of about 0.05 to about 2 microns, about 0.25 to about 1 micron, or about 0.1 to about 0.5 microns; and more preferably wherein the ferric pyrophosphate in the emulsion has an average particle size of about 0.1 to about 0.5 microns or about 0.2 to about 0.4 microns.

69. Use according to any of paragraphs 61-66, wherein the ferric pyrophosphate is in the form of a powder comprising microparticles of ferric pyrophosphate wherein the ferric pyrophosphate powder preferably has an n average particle size of about 0.025 to about 30 microns, about 0.01 to about 20 microns, about 0.05 to about 15 microns, about 0.05 to about 15 microns, about 0.25 to about 15 micron, about 0.1 to about 10 microns, about 1 to about 10 microns, or about 2 to about 10 microns; preferably wherein the ferric pyrophosphate powder has an average particle size of about 0.1 to about 10 microns, about 1 to about 10 microns, or about 2 to about 10 microns; and more preferably wherein the ferric pyrophosphate powder has an average particle size of about 1 to about 10 microns, or about 2 to about 10 microns.

70. A nutritional composition or supplement comprising:
at least one probiotic bacteria selected from the genera: *Lactobacillus, Bifidobacterium*, and *Bacillus*, and
an iron fortifying compound, wherein the iron fortifying compound comprises microparticles.

71. A nutritional composition or supplement according to paragraph 70, wherein the iron fortifying compound has a particle size distribution as defined in any of paragraphs 5-11.

72. A nutritional composition or supplement according to paragraph 70, wherein the iron fortifying compound is in the form of an emulsion with at least one fatty acid ester, and wherein the iron fortifying compound in the emulsion has an average particle size of about 0.025 to about 5 microns, about 0.01 to about 5 microns, about 0.05 to about 5 microns, about 0.05 to about 2 microns, about 0.25 to about 1 micron, or about 0.1 to about 0.5 microns; preferably wherein the iron fortifying compound in the emulsion has an average particle size of about 0.05 to about 2 microns, about 0.25 to about 1 micron, or about 0.1 to about 0.5 microns; and more preferably wherein the iron fortifying compound in the emulsion has an average particle size of about 0.1 to about 0.5 microns or about 0.2 to about 0.4 microns.

73. A nutritional composition or supplement according to paragraph 70, wherein iron fortifying compound is in the form of a powder comprising microparticles of the iron fortifying compound wherein the iron fortifying compound powder preferably has an average particle size of about 0.025 to about 30 microns, about 0.01 to about 20 microns, about 0.05 to about 15 microns, about 0.05 to about 15 microns, about 0.25 to about 15 micron, about 0.1 to about 10 microns, about 1 to about 10 microns, or about 2 to about 10 microns; preferably wherein the iron fortifying compound powder has an average particle size of about 0.1 to about 10 microns, about 1 to about 10 microns, or about 2 to about 10 microns; and more preferably wherein the iron fortifying compound powder has an average particle size of about 1 to about 10 microns, or about 2 to about 10 microns.

74. A nutritional composition or supplement according to any of paragraphs 70-73, wherein the pro biotic bacteria is a *Lactobacillus*.

75. A nutritional composition or supplement according to any of paragraphs 70-74, wherein the pro biotic bacteria comprises a species selected from the group consisting of: *L. acidophilus, L. casei, L. paracasei, L. rhamnosus, L. delbrueckii* subsp. *bulgaricus, L. brevis, L. johnsonii, L. plantarum* and *L. fermentum, L. casei* Shirota and *L. casei rhamnosus*.

76. A nutritional composition or supplement according to any of paragraphs 70-75, wherein the probiotic bacteria comprises an *L. rhamnosus* strain.
77. A nutritional composition or supplement according to any of paragraphs 70-76, wherein the *L. rhamnosus* strain is selected from the group consisting of: *L. rhamnosus* CRL1505, *L. rhamnosus* GG, *L. rhamnosus* CGMCC 1.3724 or *L. rhamnosus* NCC 4007.
78. A nutritional composition or supplement according to any of paragraphs 70-77, wherein the probiotic bacteria comprises *L. rhamnosus* CGMCC 1.3724.
79. A nutritional composition or supplement according to any of paragraphs 70-78, wherein the probiotic bacteria comprises a mixture of *L. rhamnosus* (preferably *L. rhamnosus* GG1 *L. rhamnosus* CGMCC 1.3724) and *B. lactis* (preferably *B. lactis* BB12 *B. lactis* CNCM I-3446).
80. A nutritional composition or supplement according to any of paragraphs 70-79, further comprising one or more micronutrients, preferably selected from the group consisting of vitamins, minerals and trace elements.
81. A nutritional composition or supplement according to any of paragraphs 70-80, in the form of a dietary supplement, and preferably in the form of a pre-pregnancy, or maternal (pregnancy and/or lactation) supplement.
82. A nutritional composition or supplement according to any of paragraphs 70-81, wherein the composition is solid.
83. A nutritional composition or supplement according to any of paragraphs 70-82, wherein the composition is a solid dosage form, preferably selected from the group consisting of a tablet, chewable tablet, dispersible tablet, capsule, powder, sachet containing a powder, stick-pack sachet, bottle with powder in a cap, pastille, chewing gum or lozenge.
84. A nutritional composition or supplement according to any of paragraphs 70-83, wherein the composition is a powder, preferably wherein the powder is for dispersion into a beverage.
85. A nutritional composition or supplement according to any of paragraphs 70-84, for use in: the treatment or prevention of gestational diabetes, the treatment or prevention of iron deficiency and/or the treatment or prevention of anemia in a pregnant or lactating female subject, or to a female subject prior to pregnancy.
86. A nutritional composition or supplement according to any of paragraphs 70-85 for use as an iron supplement pre-pregnancy, during pregnancy and/or during lactation.
87. A nutritional composition or supplement according to any of paragraphs 70-86 for use as a probiotic pre-pregnancy, pregnancy or lactation supplement.
88 Use of microparticulate iron compound as a fortifying agent in an oral probiotic supplement comprising at least one probiotic bacteria.
89. Use according to paragraph 88 wherein the iron compound is a ferric compound.
90. Use according to any of paragraphs 88-89, wherein the iron compound has a particle size distribution as defined in any of paragraphs 5-11.
91. Use according to any of paragraphs 88-89, wherein the iron compound is in the form of an emulsion with at least one fatty acid ester, and wherein the iron compound in the emulsion has an average particle size of about 0.025 to about 5 microns, about 0.01 to about 5 microns, about 0.05 to about 5 microns, about 0.05 to about 2 microns, about 0.25 to about 1 micron, or about 0.1 to about 0.5 microns; preferably wherein the iron compound in the emulsion has an average particle size of about 0.05 to about 2 microns, about 0.25 to about 1 micron, or about 0.1 to about 0.5 microns; and more preferably wherein the iron compound in the emulsion has an average particle size of about 0.1 to about 0.5 microns or about 0.2 to about 0.4 microns.
92. Use according to any of paragraphs 88-89, wherein iron compound is in the form of a powder comprising microparticles wherein the iron compound powder preferably has an average particle size of about 0.025 to about 30 microns, about 0.01 to about 20 microns, about 0.05 to about 15 microns, about 0.05 to about 15 microns, about 0.25 to about 15 micron, about 0.1 to about 10 microns, about 1 to about 10 microns, or about 2 to about 10 microns; preferably wherein the iron compound powder has an average particle size of about 0.1 to about 10 microns, about 1 to about 10 microns, or about 2 to about 10 microns; and more preferably wherein the iron compound powder has an average particle size of about 1 to about 10 microns, or about 2 to about 10 microns.
93. Use according to any of paragraphs 88-92, wherein the iron compound is ferric pyrophosphate.
94. Use according to any of paragraphs 88-93, wherein the probiotic bacteria comprises at least one of the genera: *Lactobacillus, Bifidobacterium*, and *Bacillus*.
95. Use according to any of paragraphs 88-94, wherein the probiotic bacteria comprises a *Lactobacillus* species.
96. Use according to paragraph 95, wherein the *Lactobacillus* is *L. rhamnosus*, preferably a strain selected rom the group consisting of: *L. rhamnosus* CRL1505, *L. rhamnosus* GG, *L. rhamnosus* CGMCC 1.3724 or *L. rhamnosus* NCC 4007, and most preferably *L. rhamnosus* CGMCC 1.3724.
97. Use according to any of paragraphs 88-96, wherein the probiotic bacteria comprises a mixture of *L. rhamnosus* (preferably *L. rhamnosus* GG1 *L. rhamnosus* CGMCC 1.3724) and *B. lactis* (preferably *B. lactis* BB12 *B. lactis* CNCM I-3446).
98 Use of a microparticulate iron compound for preserving the viability of probiotic bacteria in an oral probiotic composition.
99. Use according to paragraph 98, wherein the iron compound is a ferric compound.
100. Use according to any of paragraphs 98-99, wherein the iron compound has a particle size distribution as defined in any of paragraphs 5-11.
101. Use according to any of paragraphs 98-99, wherein the iron compound is in the form of an emulsion with at least one fatty acid ester, and wherein the iron compound in the emulsion has an average particle size of about 0.025 to about 5 microns, about 0.01 to about 5 microns, about 0.05 to about 5 microns, about 0.05 to about 2 microns, about 0.25 to about 1 micron, or about 0.1 to about 0.5 microns; preferably wherein the iron compound in the emulsion has an average particle size of about 0.05 to about 2 microns, about 0.25 to about 1 micron, or about 0.1 to about 0.5 microns; and more preferably wherein the iron compound in the emulsion has an average particle size of about 0.1 to about 0.5 microns or about 0.2 to about 0.4 microns.
102. Use according to any of paragraphs 98-99, wherein iron compound is in the form of a powder comprising microparticles of the iron compound wherein the iron compound powder preferably has an average particle size of about 0.025 to about 30 microns, about 0.01 to about 20 microns, about 0.05 to about 15 microns, about 0.05 to about 15 microns, about 0.25 to about 15 micron, about 0.1 to about 10 microns, about 1 to about 10 microns, or about 2 to about 10 microns; preferably wherein the iron compound powder has an average particle size of about 0.1 to about 10 microns, about 1 to about 10 microns, or about 2 to about 10 microns; and more preferably wherein the iron compound powder has an average particle size of about 1 to about 10 microns, or about 2 to about 10 microns.

103. Use according to any of paragraphs 98-102, wherein the iron compound is ferric pyrophosphate.
104. Use according to any of paragraphs 98-103, wherein the probiotic bacteria comprises at least one of the genera: *Lactobacillus, Bifidobacterium*, and *Bacillus*.
105. Use according to any of paragraphs 98-104, wherein the pro biotic bacteria comprises a *Lactobacillus* species.
106. Use according to paragraph 98-105, wherein the *Lactobacillus* is *L. rhamnosus*, preferably a strain selected rom the group consisting of: *L. rhamnosus* CRL1505, *L. rhamnosus* GG, *L. rhamnosus* CGMCC 1.3724 or *L. rhamnosus* NCC 4007, and most preferably *L. rhamnosus* CGMCC 1.3724.
107. Use according to any of paragraphs 98-106, wherein the pro biotic bacteria comprises a mixture of *L. rhamnosus* (preferably *L. rhamnosus* GG I IL. rhamnosus* CGMCC I. 3724) and *B. lactis* (preferably *B. lactis* BB12 *B. lactis* (NOM 1-3446).

The invention claimed is:
1. An oral composition comprising:
   at least one probiotic bacteria selected from the group consisting of: *Lactobacillus rhamnosus* CGMCC 1.3724, *Bifidobacterium lactis* CNCM I-3446, and a mixture thereof;
   ferric pyrophosphate, wherein the ferric pyrophosphate has a particle size distribution $D_{90}$ of 200 microns or less, a particle size distribution $D_{97}$ of 25 microns or less, and an average particle size of about 0.001 microns to about 10 microns; and
   at least one pharmaceutically acceptable additive or excipient selected from the group consisting of stabilizers, fillers, emulsifiers, surfactants, solubilising agents, adsorbents, flowing agents, buffers, lubricants, wetting agents, carriers, antioxidants, thickeners, anti-caking agents, coating agents, taste masking agents, preservatives, flavouring agents and dyes.
2. The composition according to claim 1, wherein the ferric pyrophosphate is in the form of a colloid.
3. The composition according to claim 1, wherein the at least one probiotic bacteria is the mixture of *Lactobacillus rhamnosus* CGMCC 1.3724 and *Bifidobacterium lactis* CNCM I-3446.
4. The composition according to claim 1, wherein the at least one probiotic bacteria comprises *Lactobacillus rhamnosus* CGMCC 1.3724.
5. The composition according to claim 1, wherein the at least one probiotic bacteria comprises *Bifidobacterium lactis* CNCM I-3446.
6. The composition according to claim 1, further comprising one or more micronutrients.
7. The composition according to claim 1, in the form of a dietary supplement.
8. The composition of claim 1, wherein the composition is an emulsion comprising at least one emulsifier.
9. The composition of claim 8, wherein the at least one emulsifier comprises at least one of fatty acid ester.
10. The composition of claim 1, wherein the particle size distribution $D_{90}$ of the ferric pyrophosphate is 100 microns or less.
11. The composition of claim 1, wherein the particle size distribution $D_{97}$ of the ferric pyrophosphate is 15 microns or less.
12. The composition of claim 1, wherein the ferric pyrophosphate has an average particle size of about 0.1 microns to about 0.5 microns.

* * * * *